United States Patent
Ceri et al.

[11] Patent Number: 6,051,423
[45] Date of Patent: Apr. 18, 2000

[54] BIOFILM ASSAY

[75] Inventors: Howard Ceri; Merle Edwin Olson, both of Calgary; Douglas Walter Morck, Airdrie; Ronald Rae Read; Andre Gerald Buret, both of Calgary, all of Canada

[73] Assignee: University Technologies International Inc., Canada

[21] Appl. No.: 09/126,957

[22] Filed: Jul. 31, 1998

Related U.S. Application Data

[62] Division of application No. 08/614,593, Mar. 13, 1996.
[51] Int. Cl.$^7$ .................................................. C12M 1/20
[52] U.S. Cl. ............................ 435/288.3; 435/287.9; 435/303.3; 435/305.3
[58] Field of Search ........................... 435/287.1, 303.3, 435/287.2, 286.7, 287.3, 287.9, 288.4, 305.3, 305.4, 299.1, 299.2

[56] References Cited

U.S. PATENT DOCUMENTS

| | | | |
|---|---|---|---|
| 2,956,931 | 10/1960 | Goldberg | 195/103.5 |
| 3,455,788 | 7/1969 | Curry et al. | |
| 3,691,988 | 9/1972 | Clarke | |
| 4,115,200 | 9/1978 | Anderson | 195/127 |
| 4,483,925 | 11/1984 | Noack | 435/293 |
| 5,017,342 | 5/1991 | Haberzettl et al. | |
| 5,326,533 | 7/1994 | Lee et al. | |
| 5,349,874 | 9/1994 | Schapira et al. | 73/864 |
| 5,462,644 | 10/1995 | Woodson | 204/131 |
| 5,605,836 | 2/1997 | Chen et al. | 435/305.4 |

FOREIGN PATENT DOCUMENTS

| | | |
|---|---|---|
| 1221896 | 6/1960 | France . |
| 2 548 685 | 1/1985 | France . |
| 1245035 | 9/1971 | United Kingdom . |
| 1522128 | 8/1978 | United Kingdom ........... G01N 33/16 |
| 83/03677 | 10/1983 | WIPO . |

OTHER PUBLICATIONS

Gjaltema, A., et al., "Heterogeneity of Biofilms in Rotating Annular Reactors: Occurrence, Structure, and Consequences", Biotech. Bioeng., 44:194–204 (1994).

Zimmerli, W., et al., "Microbiological tests to predict treatment outcome in experimental device–related infections due to *Staphylococcus aureus*", Antimicrob. Chemo., 33:959–967 (1994).

(List continued on next page.)

*Primary Examiner*—William H. Beisner
*Attorney, Agent, or Firm*—Burns, Doane, Swecker & Mathis, LLP

[57] ABSTRACT

Bacteria are incubated to form a biofilm on projections by providing a flow of liquid growth medium across projections, the direction of the flow of liquid being repeatedly changed, and an assay made of the resulting biofilm. Bacteria are incubated to form a biofilm on projections arranged in rows, with several projections in each row, while providing a flow of liquid growth medium across each row of projections, and an assay made of the resulting biofilm. Sensitivity of the biofilm to antibacterial reagent may be determined by treating the projections with antibacterial reagent before carrying out the assay, by treating each row of projections with a different antibacterial reagent, and each of the projections in a row with a different concentration of antibacterial reagent. A biofilm assay device includes a vessel including at least one channel for flow of liquid growth medium, projections arranged in at least one row and having a support for supporting the projections within the channel, and a tilt table to flow liquid growth medium along each channel in different directions across the projections. A further biofilm assay device includes a vessel including channels for flow of liquid growth medium, projections arranged in rows and having a support for supporting the projections within the channels, and a rocking table to rock the vessel and flow liquid growth medium along each channel across the projections.

9 Claims, 3 Drawing Sheets

OTHER PUBLICATIONS

Hussain, M., et al., "Radiochemical assay to measure the biofilm produced by coagulase–negative staphylococci on solid surfaces and its use to quantitate the effects of various antibacterial compounds on the formation of the biofilm", *Radiochem. Assay of Staphylococcal Biolfilm,* p. 62–69 (1991).

Evans, D.J., et al., "Susceptibility of bacterial biofilms to tobramycin: role of specific growth rate and phase in the division cycle", *J. Antimicrob. Chemo.,* 25:585–591 (1990).

Darouiche, R.O., et al., "Vancomycin Penetration into Biofilm Covering Infected Prostheses and Effect on Bacteria", *Concise Communications, JID,* 170:720–723 (1994).

Olson, M.E. et al., "Amdinocillin Treatment of Catheter–Associated Bacteriuria in Rabbits", *J. Infect. Dis.,* 159(6):1065–1072 (1989).

Morck, D.W., et al., "Therapeutic Efficacy of Fleroxacin for Eliminating Catheter–Associated Urinary Tract Infection in a Rabbit Model", *Amn. J. Med.,* 94(suppl 3A):23S–30S (1993).

Olson, M.E., et al., "Evaluation of strategies for central venous catheter replacement", *Critical Care Med.,* 20(6):797–804 (1992).

Morck, D.W., et al., "Comparative evaluation of fleroxacin, ampicillin, trimethoprim–sulfamethoxazole, and gentamicin as treatments of catheter–associated urinary tract infection in a rabbit model", *Intl. J. Antimicrob. Agents,* 4(suppl 2):S21–S27 (1994).

Costerton, J.W., et al., "Microbial Biofilms", *Anim. Rev. Microbial.,* 49:711–745 (1995).

Johnston, M.D., et al., "Disinfection tests with intact biofilms: combined use of the Modified Robbins Device with impedance detection", *J. Microbiol. Methods,* 21:15–26 (1995).

Miyake, Y., et al., "Simple Method for Measuring the Antibiotic Concentration Required to Kill Adherent Bacteria", *Microbiol. Chemo.,* 38:286–290 (1992).

Richards, G.K., et al., "An assay of *Staphylococcus epidermidis* biofilm responses to therapeutic agents", *Intl. J. Artif. Organs,* 15(11):777–787 (1993).

La Tourette Prosser, B., et al., "Method of Evaluating Effects of Antibiotics on Bacterial Biofilm", *Antimicrob. Agents Chemo.,* p. 1502–1506 (1987).

NUNC brochure, Denmark (1990).

Becton Dickinson brochure, New Jersey (date precedes filing date of patent application), no date provided.

PCT search report, no date provided.

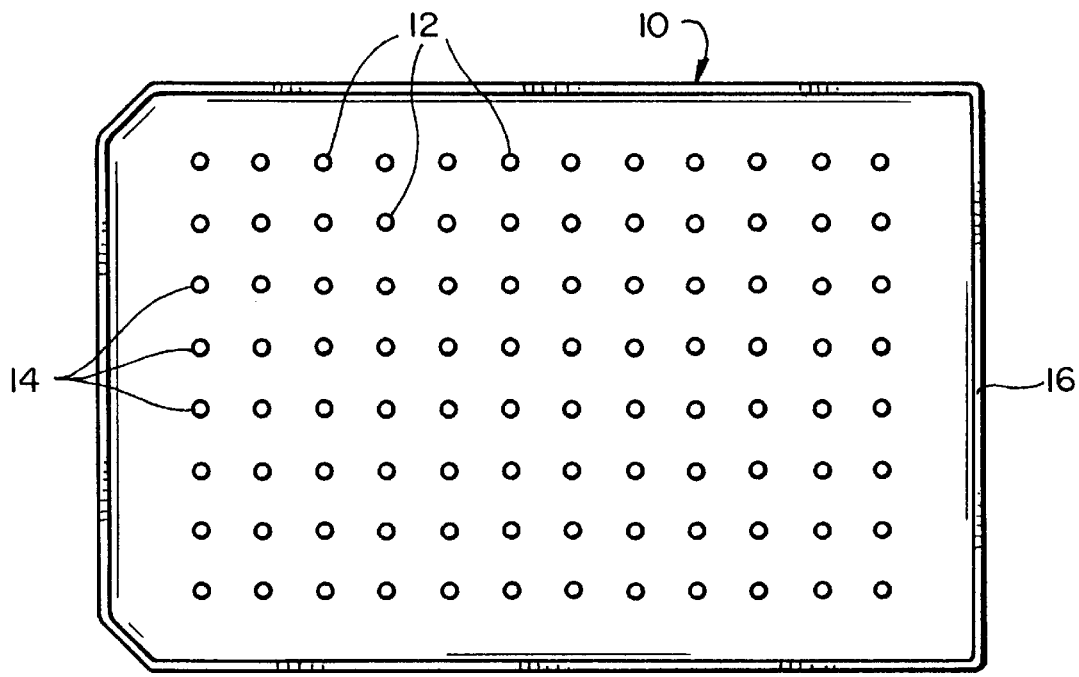
FIG_1
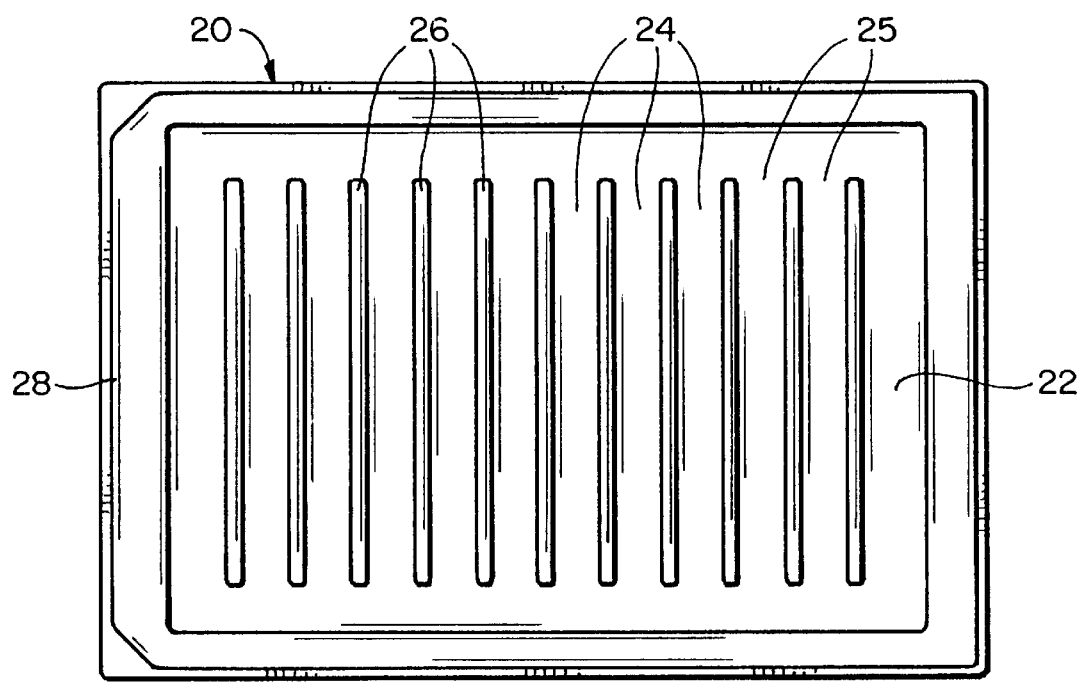
FIG_2

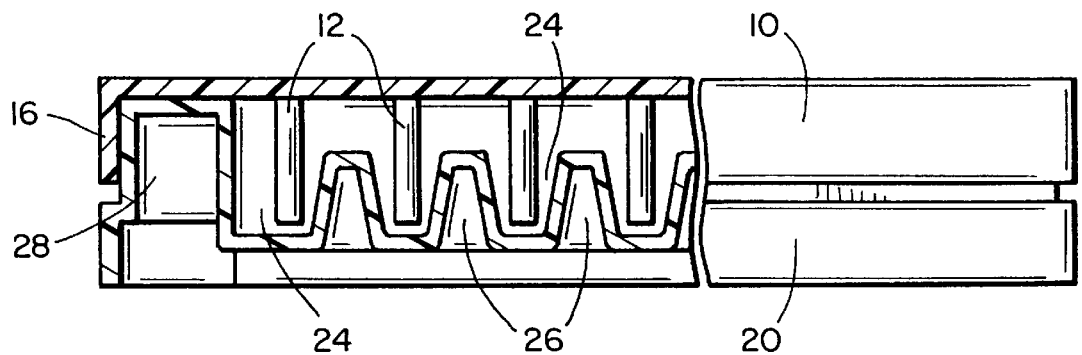
FIG_3
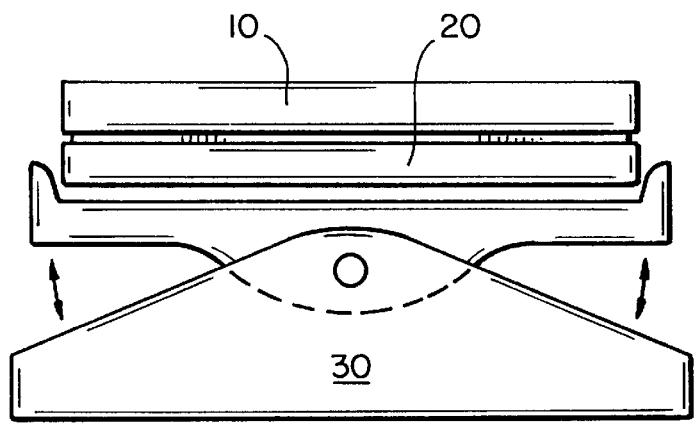
FIG_4

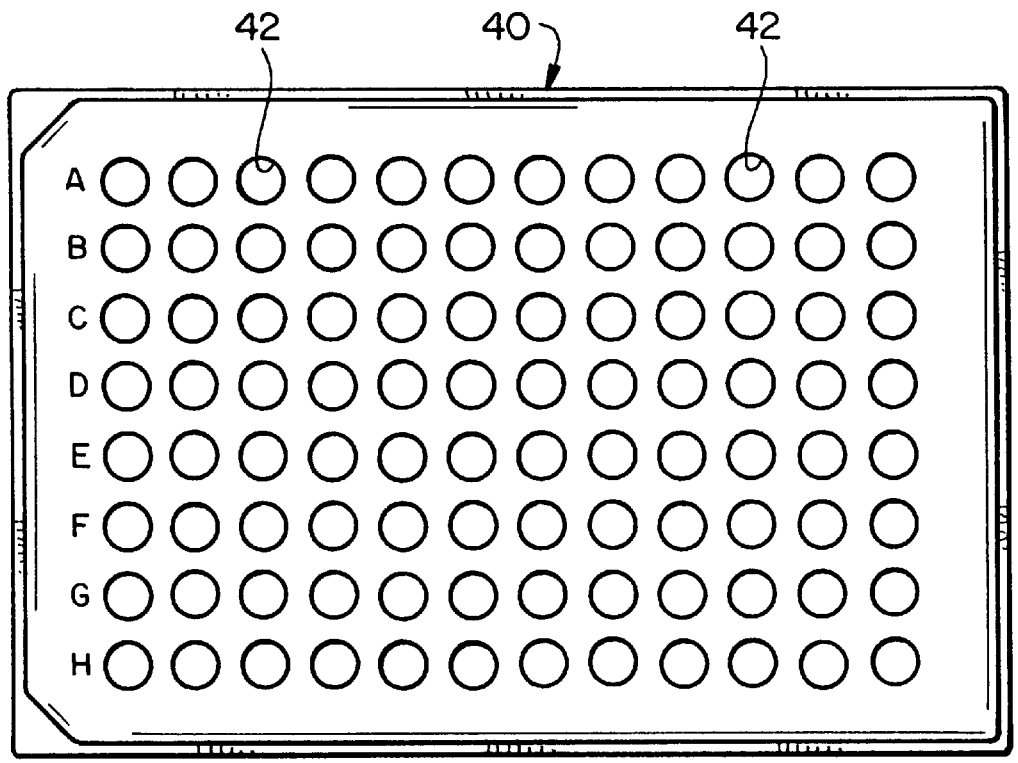
FIG_5

BIOFILM ASSAY

This application is a divisional, of application Ser. No. 08/614,593, filed Mar. 13, 1996.

FIELD OF THE INVENTION

This invention relates to methods and apparatus for the analysis of biofilms, and sensitivity of biofilms to antibacterial reagents.

BACKGROUND OF THE INVENTION

Extensive study into the growth properties of bacteria in recent years has shown that they form complex layers that adhere to surfaces. These complex forms of bacteria are known as biofilms, or sessile bacteria. Biofilms may cause problems in a variety of areas including the bodies of humans and animals, food processing, health care facilities, metal-working shops, dairy fares and other industries.

It is now widely known that bacteria in the form of biofilms are more resistant to antibacterial reagents than planktonic bacteria. Yet testing for the presence of bacteria and the testing of the efficacy of antibiotics against bacteria has traditionally involved testing for planktonic bacteria. Thus, bacterial inhibitory concentration of the antibacterial reagent may be underestimated, with the result that the wrong antibacterial reagent or wrong amount of antibacterial reagent may be used for the treatment of the bacteria.

One type of device for monitoring biofilm buildup is described in the Canadian Journal of Microbiology (1981), volume 27, pages 910 to 917, in which McCoy et al describe the use of a so-called Robbins device which comprises a tube through which water in a recycling circuit can flow. The tube has a plurality of ports in its walls, each being provided with a stud having a biofoulable surface and being capable of being retained in the port in fixed relationship with respect to the tube so that the biofoulable surface forms part of the internal surface of the tube. The studs may be removed from the ports after a desired time interval and the test surfaces by microscopy of the surfaces analyzed for the growth of microorganisms or by removal of the microorganisms from the surfaces and subsequent estimation of the degree of growth. The number of microorganisms can be estimated for instance by physical or chemical means, e.g. by detection of bacterial ATP or by further culturing the microorganisms and analyzing the products.

In another device described in U.S. Pat. No. 5,349,874, biofilm growth in a water carrying conduit is determined by providing plural removable studs in the conduit or in a second conduit parallel to the first. The studs may be removed for analysis of biofilm on the studs. Such devices as the Robbins device, or others using removable studs in a single conduit, result in rather lengthy processing times, and do not provide rapid response times for the testing of several different antibacterial reagents.

In a still further device, described in "Simple Method for Measuring the Antibiotic Concentration Required to Kill Adherent Bacteria", Miyake et al, Chemotherapy 1992; 38, 286–290, *staphylococcus aureus* cells adhered to he bottom of a 96 well plastic tissue culture plate were treated with serially diluted antibiotic solutions, and viability of the cells was judged by their growth after a further 24 hours incubation. This method has the disadvantage of inconsistent colonization of sessile bacteria and settling of planktonic bacteria.

The device described in this patent document allows for an efficient and automated biofilm killing assay that has particular use with the 96 well platform common to many diagnostic assay systems.

SUMARY OF THE INVENTION

There is therefore provided in accordance with one aspect of the invention, a method of analyzing characteristics of a biofilm, in which bacteria are incubated to form a biofilm on plural biofilm adherent sites by providing a flow of liquid growth medium across the plural biofilm adherent sites, the direction of the flow of liquid being repeatedly changed, and an assay made of the resulting biofilm.

In a further aspect of the invention, bacteria are incubated to form a biofilm on plural biofilm adherent sites arranged in plural rows, with plural biofilm adherent sites in each row, while providing a flow of liquid growth medium across the plural biofilm adherent sites, and an assay made of the resulting biofilm.

In a preferred method of the invention, the characteristic of the biofilm is the sensitivity of the biofilm to antibacterial reagent and the method further includes, before assaying the biofilm, treating the biofilm adherent sites with antibacterial reagent.

In a further aspect of the invention, there is also included the step of, after treating the biofilm adherent sites with antibacterial reagent, dislodging the biofilm from the biofilm adherent sites and further incubating the biofilm. Dislodging the biofilm from the biofilm adherent sites may include dislodging the biofilm from each biofilm adherent site into a separate well of a microtiter plate.

When the biofilm adherent sites are formed in rows, treating the biofilm adherent sites with an antibacterial reagent may include treating each row of biofilm adherent sites with a different antibacterial reagent, and treating each of the biofilm adherent sites in a row with a different concentration of antibacterial reagent.

Preferably, the flow direction of the liquid growth medium is repeatedly reversed. In this aspect of the invention, the liquid growth medium may flow in channels of a vessel, and the direction of flow of the liquid growth medium is reversed by rocking of the vessel.

In a further aspect of the invention, the biofilm adherent sites are projections from a lid and incubating the biofilm includes suspending the projections in liquid growth medium in the channels while rocking the vessel so as to provide shear forces on the biofilm during growth of the biofilm.

There is further provided, in accordance with an aspect of the invention, apparatus for analyzing biofilms, the apparatus comprising:

a vessel including at least one channel for flow of liquid growth medium;

plural biofilm adherent sites arranged in at least one row and having a support for supporting the plural biofilm adherent sites within the channel; and means to flow liquid growth medium along each channel in different directions across the plural biofilm adherent sites.

In accordance with a still further aspect of the invention, there is provided apparatus for analyzing biofilms, the apparatus comprising:

a vessel including plural channels for flow of liquid growth medium;

plural biofilm adherent sites arranged in plural rows and having a support for supporting the plural biofilm adherent sites within the channels; and means to flow liquid growth medium along each channel across the plural biofilm adherent sites.

Preferably, the plural biofilm adherent sites are formed in plural rows, with plural sites in each row; and the vessel includes plural channels, with one channel for each row of plural biofilm adherent sites.

In a further aspect of the invention, the support for the plural biofilm adherent sites forms a lid for the vessel.

In a still further aspect of the invention, the means to flow liquid growth medium across the plural biofilm adherent sites is a tilt table.

These and other aspects of the invention will be made apparent in the description and claims that follow.

BRIEF DESCRIPTION OF THE DRAWINGS

There will now be described preferred embodiments of the invention, with reference to the drawings, by way of illustration, in which like numerals denote like elements and in which:

FIG. 1 is a bottom view of plural biofilm adherent sites on a lid of a vessel;

FIG. 2 is a top view of a vessel for receiving the plural biofilm adherent sites of FIG. 1;

FIG. 3 is a side view, partly broken away, of the lid and vessel of FIGS. 1 and 2;

FIG. 4 is a side view schematic of a lid and vessel combination as shown in FIG. 3 on a tilt table; and FIG. 5 is a top view of a 96 well plate for use with the invention.

DETAILED DESCRIPTION OF PREFERRED EMBODIMENTS

As shown most particularly in FIGS. 1, 2 and 3, the biofilm assay device includes a biofilm lid 10 composed of ELISA grade plastic or other suitable material (eg. stainless steel, titanium) with projections 12 from the lid 10. The projections 12 form biofilm adherent sites to which a biofilm may adhere. The projections 12 are preferably formed in at least eight rows 14 of at least twelve projections each. Other numbers of rows or numbers of projections in a row may be used, but this is a convenient number since it matches the 96 well plates commonly used in biomedical devices. Additional projections as shown may be used to determine the initial biofilm concentration after incubation. The exemplary projections 12 shown are about 1.5 cm long and 2 mm wide.

The biofilm assay device also includes a vessel 20 which includes a liquid holding basin 22 divided into plural channels (troughs) 24 by moulded ridges 26. The channels 24 are wide enough to receive the projections 12. There should be one channel 24 for each projection 12 of any given row 14. The lid 10 forms a support for the projections 12 for supporting the biofilm adherent sites within the channels 24. The lid 10 has a surrounding lip 16 that fits tightly over a surrounding wall 28 of the vessel 20 to avoid contamination of the inside of the vessel during incubation.

The biofilm incubation vessel 20 serves two important functions for biofilm development, The first is as a reservoir for liquid growth medium containing the bacterial population which will form a biofilm on the projections 12 of the biofilm lid 10. The second function is to generate shear force across the projections, which allows for optimal biofilm production on the projections.

As shown, in FIG. 4, shear force on the projections 12 is generated by rocking the vessel 20 with lid 10 on a tilt table 30. The projections 12 sit suspended in the channels 24, so that the tips of the projections 12 may be immersed in liquid growth medium flowing in the channels 24. The ridges 26 channel the liquid growth medium along the channels 24 past and across the projections 12, and thus generate a shear force across the projections. Rocking of the vessel 10 causes a repeated change in direction of flow, in this case a repeated reversal of flow of liquid growth medium, across the projections 10, which helps to ensure a biofilm of equal proportion on each of the projections 12 of the lid 10. While it is possible to grow biofilm with only one direction of flow of liquid growth medium, the use of an array of projections 12 suspended in several channels makes the arrangement difficult to construct, since then some method would need to be found to recirculate fluid around from one end of each channel to the other end. Rocking of the vessel, with liquid flowing backwards and forwards along the channels, provides an excellent biofilm growth environment that simulates natural occurring conditions of turbulent flow.

Each projection 12 and each channel 24 should have substantially the same shape (within manufacturing tolerances) to ensure uniformity of shear flow across the projections during biofilm formation. In addition, the uniform channels 24 should all be connected so that they share the same liquid nutrient and bacterial mixture filling the basin 22. With sharing of the same bacterial soup and channel configuration being the same for each channel, biofilms are produced at each projection that are equivalent for the purpose of testing antibacterial reagents. In this way, different concentrations of different antibiotics may be compared to each other without regard to positional variance of the projections. Biofilms thus produced are considered to be uniform. Results have been obtained within $P<0.05$ for random projections on the plate.

Sensitivity of a biofilm to antibiotic or biocide, referred to in this patent document collectively as "antibacterial reagent", is measured by treating the biofilm adherent sites with an anti-bacterial reagent, and then assaying the biofilm. This may be accomplished by placing the lid 10, which was colonized with a bacterial biofilm in an incubation vessel 12, into a conventional 96 well plate 40 such as illustrated in FIG. 5, the number of wells 42 being determined by the number of projections 12, in which growth medium containing antibiotic or biocide dilutions has been dispensed. The lid 10 and plate 40 fit such that bacterial contamination from outside the plate cannot take place. Projections 12 that have been incubated in the same channel 24 of the vessel 20 should each be treated with a different anti-bacterial reagent. In this manner, consistent results may be obtained since the growth conditions in any one channel will be very similar along the entire channel and thus for each projection 12 suspended in that channel. This helps improves the reliability of treatment of different projections 12 with different anti-bacterial reagents.

In addition, for the step of incubating the biofilm after treatment with an antibacterial reagent, a conventional cover (not shown) made of the same plastic as the 96 well plate 40 is required so as to prevent contamination of the 96 well plates 40 during incubation and to form a very low profile with the plate 40 as to make the covered plate accessible to standard ELISA plate readers. For each assay, two 96 well plates 40 and plate covers will be needed to provide the traditional Minimum Inhibitory Concentration (MIC) and the Minimum Biofilm Eliminating Concentration (MBEC).

Procedure

For each organism a biofilm growth curve should be determined to ensure the biofilm has reached satisfactory proportion to be tested for antibiotic/biocide sensitivity.

Day 1—incubate bacteria of choice in a suitable growth medium, which may be tryptic soy broth (TSB), overnight with shaking at a suitable incubation temperature under optimal oxygen tension. The temperature may be, in each case of incubation described in this patent disclosure, 37° C.

Day 2—Fill the vessel 20 of the biofilm assay device system with 20 ml of a 2% overnight culture suspended in fresh growth medium (eg TSB); cover with projection covered lid 10 and incubate on a rocking platform (Bellco Rocker Platform), for example at setting 3 in a 37° C. incubator. Aseptically remove 2 projections per hour starting at hour 2 of the growth curve and continuing for 7 hours. Each projection is rinsed by gentle dipping in sterile phosphate buffered saline (PBS), and then placed in 1 ml of sterile phosphate buffered saline and sonicated for 5 min. using a DoALL Ultrasonic Cleaner at 21 kc to dislodge the biofilm. The sonicate is serially diluted ($10^{-1}$ through $10^{-6}$) in phosphate buffered saline and spot plated to determine biofilm count.

Day 3—Plates are counted to determine the rate of colonization and to calculate the incubation time required to achieve a biofilm of $\sim 10^5$ colony forming units (cfu)/projection, which is an optimal biofilm thickness for measuring antibiotic/biocide killing.

MBEC Assay

Day 1—Inoculate growth medium (eg TSB) with bacteria and grow overnight, for example at 37° C. with shaking.

Day 2

(1) Place 20 ml of a 2% overnight culture diluted in fresh growth medium (for example TSB) in the vessel 20 of the biofilm assay device system, cover with the biofilm lid 10 and incubate on the rocking platform 30, for example at 37° C. for the time required to reach a biofilm of $\sim 10^5$ cfu/projection 12. Change of direction of flow of liquid growth medium caused by the rocking of the tilt table 30 enhances the growth of a biofilm.

(2) While the biofilm is incubating, in a sterile hood prepare antibiotic stock solutions at 5 mg/ml in sterile double distilled water (ddw) or biocide as per directions of the producer, and prepare antibiotic/biocide dilutions in growth medium (for example TSB) in a 96 well plate. Up to 8 different antibiotics or biocides can be tested by using 1 row (A–H) for each antibacterial reagent. Plates are set up as follows:

Rows A–H each contain a specific antibiotic/biocide.
Wells in each row are set up with different concentrations of antibacterial reagent as follows:
Well #1 TSB no antibiotic
Well #2 TSB plus 1 mg/ml antibiotic
Well #3 TSB plus $2^{-2}$ mg/ml antibiotic
Well #4 TSB plus $2^{-3}$ mg/ml antibiotic
Well #5 TSB plus $2^{-4}$ mg/ml antibiotic
Well #6 TSB plus $2^{-5}$ mg/ml antibiotic
Well #7 TSB plus $2^{-6}$ mg/ml antibiotic
Well #8 TSB plus $2^{-7}$ mg/ml antibiotic
Well #9 TSB plus $2^{-8}$ mg/ml antibiotic
Well #10 TSB plus $2^{-9}$ mg/ml antibiotic
Well #11 TSB plus $2^{-10}$ mg/ml antibiotic
Well #12 TSB plus $2^{-11}$ mg/ml antibiotic (3) After the incubation period, break off 2 projections 12 (from an area of lid 10 that will not be used in the antibiotic assay, i.e. an unused row) rinse and a sonicate in PBS, dilute and spot on plates to determine the initial biofilm concentration (exactly as done on the growth curve). Rinse the remaining projections in PBS using a troughed vessel 20 and place the colonized projections into the 96 well antibiotic plate and incubate overnight at 37° C.

Day 3

Depending on the technology used to assay the incubated and treated biofilm, the biofilm may be assayed in place, without dislodging, or may be dislodged from the projections and then assayed, or may be dislodged, further incubated and then assayed. The following steps show an example in which the biofilm is dislodged, incubated and assayed.

(1) In a sterile hood remove biofilm lid 10 from the 96 well antibiotic plate (do not discard the plate), rinse the projections in a 96 well plate containing sterile PBS, then place the lid 10 in a fresh 96 well plate containing fresh TSB (0.25 ml per well) and sonicate the entire biofilm lid 10 to dislodge the surviving biofilm bacteria, with the biofilm from any one projection 12 being dislodged into a separate well of the 96 well plate. Again in the hood remove the biofilm lid 10 and replace with a flat cover.

(2) Read the antibiotic plate at 490 nm for indication of planktonic survival, or use some other method, such as are known in the art, for assaying planktonic survival.

(3) From the freshly sonicated plate remove 0.02 ml of the medium from each well and spot plate neat; and 0.025 ml from each well to prepare a serial dilution ($10^{-1}$ to $10^{-6}$) and spot plate 0.02 ml (dilutions can be done in microtiter plates, one for each antibiotic). Place the plate containing the remaining medium and bacteria to incubate at 37° C., overnight.

Day 4

Assay the sessile survival, by for example reading the plate incubated overnight at 490 nm or by counting the colonies on the plates to determine the actual number of surviving bacteria, or by using some other method known in the art.

Several different conventional methods may be used to count the bacteria. It may be done by incubating the sonicated bacteria, taking serial dilutions and visually counting the colony forming units, or automated methods may be used, as for example using an optical reader to determine optical density. It has been found however that the optical reader of turbidity is too imprecise for practical application, and it is preferred that vital dye technology be applied to automate the measurement of viability, by treating the biofilm with a vital dye, and measuring the intensity of light given off by the dyed biofilm. In the case of using vital dye technology, the biofilm need not be further incubated. In a further embodiment, the assay may be carried out by sonicating the cells until they lyse and release ATP and then adding luciferase to produce a mechanically readable light output. In a still further embodiment, the assay may be carried out directly on the biofilm on the projections using a confocal microscope, although it should be considered that this is difficult to automate. In the examples that follow, the results are obtained from a manual count following serial dilution. Examples are given to show a comparison between counts of planktonic bacteria and counts of sessile bacteria for the same growth conditions.

EXAMPLE #1

Table 1 shows the results or incubation of *staphylococcus epidermidis* biofilm on projections 12 in channels 24 while rocking the vessel 20, followed by treatment with antibiotics A (Ancef, cefazolin), B (Orbenin-2000, cloxacillin), C (Primaxin, imipenem and cilastatin), D (Vancomycin), E (Dalacin, clindamycin) and F (Tazadine, ceftazidine) in doubling dilutions. The antibiotic was applied to the wells 2–12 in rows A–F of a 96 well plate as follows: well 2: no antibiotic, well 3: 1000 µg/mL, well 4: 500 µg/mL . . . well 12: 2 µg/mL. Results are given in Table 1 terms of cfu/projection from a manual reading.

rocking the vessel 20, followed by treatment with antibiotics A (Ancef, cefazolin), B (Orbenin-2000, cloxacillin), C (Primaxin, imipenem and cilastatin), D (Vancomycin), E (Dalacin, clindamycin) F (Tazadine, ceftazidine) and G (Ciprofloxacin) in doubling dilutions. The antibiotic was applied to the wells 2–12 of the rows A–G of a 96 well plate as follows: well 2: no antibiotic, well 3: 1000 µg/mL, well 4: 500 µg/mL . . . well 12: 2 µg/mL.

TABLE 1

|   | 2 | 3 | 4 | 5 | 6 | 7 | 8 | 9 | 10 | 11 | 12 |
|---|---|---|---|---|---|---|---|---|----|----|----|
| A | $5.5 \times 10^4$ | $1.1 \times 10^4$ | $4.5 \times 10^3$ | $4.0 \times 10^3$ | $4.5 \times 10^3$ | $1.2 \times 10^4$ | $6.0 \times 10^4$ | $5.5 \times 10^4$ | $3.0 \times 10^5$ | $1.4 \times 10^5$ | $2.1 \times 10^5$ |
| B | $1.7 \times 10^4$ | $6.0 \times 10^2$ | $1.1 \times 10^3$ | $1.2 \times 10^3$ | $2.0 \times 10^3$ | $2.0 \times 10^3$ | $2.2 \times 10^4$ | $1.6 \times 10^3$ | $1.6 \times 10^4$ | $2.6 \times 10^4$ | $9.5 \times 10^4$ |
| C | $9.0 \times 10^3$ | $8.5 \times 10^2$ | $1.2 \times 10^3$ | $1.9 \times 10^3$ | $3.2 \times 10^4$ | $6.5 \times 10^4$ | $5.5 \times 10^4$ | $6.5 \times 10^4$ | $1.0 \times 10^5$ | $1.5 \times 10^5$ | $1.1 \times 10^6$ |
| D | $1.2 \times 10^4$ | $1.1 \times 10^3$ | $7.0 \times 10^2$ | $1.3 \times 10^3$ | $1.9 \times 10^3$ | $6.5 \times 10^3$ | $8.0 \times 10^3$ | $2.5 \times 10^3$ | $2.5 \times 10^3$ | $5.0 \times 10^3$ | $2.5 \times 10^5$ |
| E | $1.0 \times 10^4$ | $3.5 \times 10^3$ | $6.5 \times 10^3$ | $5.0 \times 10^3$ | $1.2 \times 10^4$ | $1.0 \times 10^4$ | $7.5 \times 10^4$ | $8.0 \times 10^4$ | $2.5 \times 10^4$ | $8.5 \times 10^4$ | $1.9 \times 10^6$ |
| F | $5.5 \times 10^4$ | $1.9 \times 10^3$ | $2.3 \times 10^3$ | $4.5 \times 10^3$ | $3.5 \times 10^4$ | $1.4 \times 10^4$ | $1.9 \times 10^5$ | $2.5 \times 10^4$ | $4.0 \times 10^4$ | $3.5 \times 10^4$ | $2.7 \times 10^5$ |

Table 2 gives the optical density readings of turbidity of the same *staphylococcus epidermidis* biofilm, treated in the same manner as the samples of Table 1, to show a comparison between the manually counted cfu and the —automated reading.

TABLE 2

|   | 2 | 3 | 4 | 5 | 6 | 7 | 8 | 9 | 10 | 11 | 12 |
|---|---|---|---|---|---|---|---|---|----|----|----|
| A | .951 | .856 | .971 | 1.010 | .961 | .984 | .993 | 1.036 | .996 | .967 | .980 |
| B | .900 | .935 | .890 | .915 | .902 | .998 | .944 | .919 | .909 | .963 | .938 |
| C | .914 | .843 | .768 | .792 | .870 | .907 | .869 | .927 | .863 | .908 | .959 |
| D | .898 | .524 | .708 | .805 | .884 | .898 | .854 | .835 | .901 | .907 | .958 |
| E | .901 | .869 | .894 | .851 | .858 | .936 | .873 | .907 | .874 | .937 | .938 |
| F | .905 | .897 | .888 | 1.013 | .855 | .992 | .903 | .920 | .850 | .843 | .902 |

Table 3 shows the optical density readings of turbidity of *staphylococcus epidermidis* planktonic bacteria incubated and treated with antibacterial reagent under the same conditions as for the results shown in Table 1. This table clearly shows how the assay of planktonic bacteria gives a lower count in many instances than the assay of sessile bacteria incubated and treated under the same conditions.

TABLE 3

|   | 2 | 3 | 4 | 5 | 6 | 7 | 8 | 9 | 10 | 11 | 12 |
|---|---|---|---|---|---|---|---|---|----|----|----|
| A | .959 | .353 | .381 | .411 | .403 | .409 | .413 | .411 | .599 | .574 | .610 |
| B | .927 | .346 | .375 | .400 | .404 | .442 | .422 | .408 | .430 | .562 | .585 |
| C | .950 | .409 | .411 | .431 | .426 | .447 | .475 | .476 | .504 | .553 | .620 |
| D | .907 | .351 | .374 | .403 | .410 | .409 | .421 | .404 | .415 | .413 | .406 |
| E | .903 | .861 | .845 | .907 | .913 | .887 | .959 | .878 | .910 | .890 | .929 |
| F | .905 | .359 | .383 | .397 | .410 | .466 | .540 | .615 | .627 | .694 | .853 |

EXAMPLE #2

Table 4 shows the results of incubation of *staphylococcus aureus* biofilm on projections 12 in channels 24 while

TABLE 4

|   | 2 | 3 | 4 | 5 | 6 | 7 | 8 | 9 | 10 | 11 | 12 |
|---|---|---|---|---|---|---|---|---|---|---|---|
| A | $2.0 \times 10^5$ | 0 | 0 | 0 | 50 | 50 | 50 | 50 | $5.0 \times 10^2$ | $1.0 \times 10^4$ | $2.0 \times 10^4$ |
| B | $5.0 \times 10^5$ | 0 | 50 | 0 | 0 | 50 | $1.0 \times 10^3$ | 0 | $4.5 \times 10^2$ | 50 | $9.0 \times 10^2$ |
| C | $1.5 \times 10^5$ | 0 | 0 | 0 | 0 | 0 | 0 | 0 | 0 | 0 | $1.0 \times 10^2$ |
| D | $6.0 \times 10^5$ | 0 | 0 | 0 | 0 | 0 | 0 | 0 | 0 | 0 | $1.5 \times 10^4$ |
| E | $4.5 \times 10^5$ | 0 | 0 | 0 | 0 | 0 | $5.0 \times 10^2$ | 50 | 0 | 0 | $2.0 \times 10^3$ |
| F | $2.0 \times 10^5$ | 0 | $1.0 \times 10^2$ | 0 | $1.0 \times 10^2$ | 50 | 0 | 0 | $1.0 \times 10^5$ | $4.0 \times 10^5$ | $9.0 \times 10^5$ |
| G | $3.5 \times 10^5$ | 0 | 0 | 0 | 50 | $1.0 \times 10^2$ | 50 | 0 | 0 | 0 | 0 |

Table 5 shows the optical density readings of turbidity of the same *staph. aureus* biofilm, treated in the same manner as the samples of Table 4, to show a comparison between the manually counted cfu and the automated reading.

TABLE 5

|   | 2 | 3 | 4 | 5 | 6 | 7 | 8 | 9 | 10 | 11 | 12 |
|---|---|---|---|---|---|---|---|---|---|---|---|
| A | .963 | .333 | .414 | .461 | .758 | .666 | .647 | .649 | .673 | .845 | .853 |
| B | .924 | .073 | .626 | .072 | .791 | .771 | .832 | .071 | .803 | .858 | .838 |
| C | .913 | .073 | .073 | .071 | .073 | .073 | .071 | .072 | .071 | .617 | .822 |
| D | .903 | .073 | .073 | .071 | .093 | .071 | .071 | .070 | .071 | .073 | .903 |
| E | .942 | .073 | .074 | .070 | .071 | .072 | .487 | .627 | .069 | .096 | .867 |
| F | .938 | .779 | .830 | .777 | .739 | .719 | .840 | .806 | .882 | .924 | .916 |
| G | .929 | .073 | .072 | .073 | .778 | .822 | .793 | .121 | .071 | .072 | .068 |

Table 6 shows the optical density readings of turbidity of *staph. aureus* planktonic bacteria incubated and treated with antibacterial reagent under the same conditions as for the results shown in Table 4. This table clearly shows how the assay of planktonic bacteria gives a lower count in many instances than the assay of sessile bacteria incubated and treated under the same conditions.

TABLE 6

|   | 2 | 3 | 4 | 5 | 6 | 7 | 8 | 9 | 10 | 11 | 12 |
|---|---|---|---|---|---|---|---|---|---|---|---|
| A | .935 | .064 | .061 | .065 | .067 | .066 | .067 | .068 | .063 | .058 | .057 |
| B | .691 | .070 | .071 | .077 | .071 | .069 | .069 | .073 | .068 | .067 | .059 |
| C | .880 | .116 | .106 | .097 | .087 | .081 | .078 | .078 | .081 | .074 | .072 |
| D | .891 | .071 | .074 | .081 | .077 | .075 | .078 | .078 | .076 | .075 | .075 |
| E | .857 | .069 | .074 | .080 | .077 | .080 | .075 | .078 | .076 | .084 | .264 |
| F | .895 | .073 | .076 | .081 | .079 | .076 | .079 | .078 | .111 | .564 | .717 |
| G | .895 | .094 | .072 | .077 | .077 | .079 | .077 | .077 | .080 | .074 | .069 |

EXAMPLE #3

Table 7 shows the results of incubation of *Escherichia coli* biofilm on projections 12 in channels 24 while rocking the vessel 20, followed by treatment with antibiotics A (Ticarcillin, Sigma T-5639), B (Carbenicillin, Sigma C-1389), C (Tobramycin, Sigma T-4014), D (Gentamicin sulphate, Sigma G-3632), E (Ampicillin, Sigma A-9518), F (Tazadine, ceftazidine), G (Primaxin, imipenem and cilastatin) and H (Ciprofloxacin) in doubling dilutions. The *Escherichia coli* was started with an inoculum of 2% of overnight growth in fresh TSB. 20 ml were placed in the main basin of the vessel 20 (channels 2–12), with 1.5 ml in the channel 1 to provide a sampling of initial colonization on the projections of the first row. The initial biofilm was colonized for four hours. The antibiotic was applied to the wells 2–12 of the rows A–H of a 96 well plate as follows: well 2: no antibiotic, well 3: 1000 µg/mL, well 4: 500 µg/mL . . . well 12: 2 µg/mL. 250 µL final volume of diluted antibiotic was applied to the wells.

TABLE 7

|   | 2 | 3 | 4 | 5 | 6 | 7 | 8 | 9 | 10 | 11 | 12 |
|---|---|---|---|---|---|---|---|---|---|---|---|
| A | $1.9 \times 10^5$ | 0 | 0 | 0 | 0 | 0 | $3.5 \times 10^2$ | $2.0 \times 10^2$ | $2.5 \times 10^2$ | $1.5 \times 10^4$ | $3.0 \times 10^4$ |
| B | $2.0 \times 10^8$ | $1.5 \times 10^2$ | 0 | 0 | 0 | $1.5 \times 10^2$ | 0 | $2.0 \times 10^2$ | $2.0 \times 10^3$ | $1.2 \times 10^5$ | $1.1 \times 10^7$ |
| C | $1.0 \times 10^7$ | 0 | 0 | 0 | 0 | 0 | 0 | 0 | $2.5 \times 10^4$ | $1.1 \times 10^6$ | $1.3 \times 10^7$ |
| D | $1.5 \times 10^7$ | 0 | 0 | 0 | 0 | 0 | 0 | 0 | $1.5 \times 10^3$ | $1.5 \times 10^6$ | $2.5 \times 10^6$ |
| E | $8.5 \times 10^7$ | $2.0 \times 10^5$ | 0 | $1.1 \times 10^5$ | $4.0 \times 10^5$ | $2.0 \times 10^6$ | 0 | $1.5 \times 10^5$ | $8.5 \times 10^5$ | $6.5 \times 10^7$ | $5.0 \times 10^7$ |
| F | $1.2 \times 10^8$ | 0 | 0 | 0 | 0 | 0 | 0 | 0 | $2.0 \times 10^3$ | $1.5 \times 10^4$ | $1.5 \times 10^4$ |

TABLE 7-continued

|   | 2 | 3 | 4 | 5 | 6 | 7 | 8 | 9 | 10 | 11 | 12 |
|---|---|---|---|---|---|---|---|---|---|---|---|
| G | $1.0 \times 10^7$ | 0 | 0 | $2.0 \times 10^2$ | 0 | 0 | 0 | 0 | 0 | 0 | 0 |
| H | $1.1 \times 10^3$ | 0 | 0 | 0 | 0 | 0 | 0 | $1.5 \times 10^2$ | 0 | 0 | $2.0 \times 10^2$ |

Table 8 shows the optical density readings of turbidity of the same *Escherichia coli* biofilm, treated in the same manner as the samples of Table 7, to show a comparison between the manually counted cfu and the automated reading.

TABLE 8

|   | 2 | 3 | 4 | 5 | 6 | 7 | 8 | 9 | 10 | 11 | 12 |
|---|---|---|---|---|---|---|---|---|---|---|---|
| A | 1.296 | .120 | .118 | .121 | 1.064 | 1.099 | .661 | 1.097 | 1.130 | 1.244 | 1.250 |
| B | 1.328 | 1.181 | .669 | 1.247 | .876 | .759 | .653 | 1.114 | 1.177 | 1.192 | 1.297 |
| C | 1.289 | .121 | .122 | .121 | .122 | .122 | .119 | .666 | .647 | .829 | 1.299 |
| D | 1.260 | .124 | .121 | .123 | .121 | .132 | .123 | .672 | 1.184 | 1.296 | 1.294 |
| E | 1.345 | 1.053 | .124 | 1.046 | 1.114 | 1.544 | .797 | 1.334 | 1.303 | 1.573 | 1.332 |
| F | 1.341 | .121 | .123 | 1.158 | .121 | .125 | .120 | .123 | 1.152 | 1.249 | 1.268 |
| G | 1.313 | .124 | 1.142 | 1.215 | 1.235 | 1.284 | .773 | 1.180 | 1.117 | 1.274 | .637 |
| H | 1.317 | .122 | .126 | .118 | .119 | .123 | .786 | 1.011 | .969 | .940 | 1.233 |

Table 9 shows the optical density readings of turbidity of *Escherichia coli* planktonic bacteria incubated and treated with antibacterial reagent under the same conditions as for the results shown in Table 7. This table clearly shows how the assay of planktonic bacteria gives a lower count in many instances than the assay of sessile bacteria incubated and treated under the same conditions.

TABLE 9

|   | 2 | 3 | 4 | 5 | 6 | 7 | 8 | 9 | 10 | 11 | 12 |
|---|---|---|---|---|---|---|---|---|---|---|---|
| A | 1.080 | .119 | .132 | .137 | .135 | .137 | .138 | .154 | .143 | .159 | .273 |
| B | 1.212 | .120 | .135 | .134 | .134 | .132 | .137 | .136 | .185 | .252 | .652 |
| C | .828 | .122 | .132 | .136 | .136 | .133 | .141 | .133 | .588 | .601 | .873 |
| D | 1.040 | .125 | .133 | .138 | .135 | .141 | .141 | .136 | .334 | .837 | .936 |
| E | 1.040 | .124 | .129 | .133 | .138 | .142 | .139 | .254 | .231 | .629 | 1.425 |
| F | 1.098 | .123 | .129 | .134 | .137 | .128 | .137 | .137 | .140 | .147 | .152 |
| G | .560 | .206 | .190 | .177 | .161 | .146 | .148 | .141 | .135 | .139 | .153 |
| H | 1.147 | .131 | .136 | .136 | .140 | .132 | .139 | .136 | .138 | .133 | .138 |

The concentration (MBEC) of anti-bacterial reagent at which the survival of bacteria falls to zero may be assessed readily from the assay. Likewise, the MIC may also be determined from the assay.

The inventors have found that in some instances a biofilm will not form without the inclusion of host components in the biofilm. Host components may therefore be added to the growth medium in the vessel during incubation of the bacteria to form the biofilm. Host components that may be added include serum protein and cells from a host organism. For the testing of the effect of different host cells and components, the ends 25 of the channels 24 may be sealed by walls to prevent growth medium in one channel from flowing into another, thus isolating the bacteria growth in each channel from other channels.

The device thus described may also be used to test coatings used to inhibit biofilm growth and to test coatings which may enhance biofilm formation. In an initial step, the projections 12 may be coated with a coating to be tested, and then the biofilm grown on the projections. The biofilm may then be assayed, or treated with anti-bacterial reagent and then assayed. The assay may be in situ or after dislodging of the biofilm. Different coatings may be tested on different rows of pegs. Enhanced biofilm formation may be used to create large viable biofilms for bio-fermentation.

While the preferred technique is to reverse flow of the liquid growth medium, the array could have a unidirectional flow of liquid, with recircling of fluid from one end of each channel to the other end of the same channel, but this complicates the arrangement A person skilled in the art could make immaterial modifications to the invention described in this patent document without departing from the essence of the invention that is intended to be covered by the scope of the claims that follow.

The embodiments of the invention in which an exclusive property or privilege is claimed are defined as follows:

1. Apparatus for analyzing biofilms, the apparatus comprising:
   a vessel including at least on channel for flow of liquid growth medium;
   plural biofilm adherent sites having a support for supporting the plural biofilm adherent sites within the channel;
   means to flow liquid growth medium along each channel in different directions across the plural biofilm adherent sites;
   the plural biofilm adherent sites are formed in plural rows, with more than one biofilm adherent site in each row; and
   the vessel includes plural channels having substantially the same shape.

2. The apparatus of claim 1 in which the biofilm adherent sites have substantially the same shape.

3. The apparatus of claim 2 in which:

the support for the plural biofilm adherent sites forms a lid for the vessel.

4. The apparatus of claim 2 in which the means to flow liquid growth medium across the plural biofilm adherent sites is a tilt table.

5. The apparatus of claim 1 in which the means to flow liquid growth medium across the plural biofilm adherent sites is a tilt table.

6. Apparatus for analyzing biofilms, the apparatus comprising:

a vessel including plural channels for flow of liquid growth medium, each of said channels having substantially the same shape;

plural biofilm adherent sites arranged in plural rows and having a support for supporting the plural biofilm adherent sites within the channels, each of said sites having substantially the same shape; and means to flow liquid growth medium along each channel across the plural biofilm adherent sites supported within the channel.

7. The apparatus of claim 6 in which the means to flow liquid growth medium along each channel across the plural biofilm adherent sites is a tilt table.

8. The apparatus of claim 6 in which the support for the plural biofilm adherent sites forms a lid in the vessel.

9. The apparatus of claim 8 in which the plural biofilm adherent sites are projections from the lid.

* * * * *

UNITED STATES PATENT AND TRADEMARK OFFICE
CERTIFICATE OF CORRECTION

PATENT NO. : 6,051,423
DATED : April 18, 2000
INVENTOR(S) : Ceri et al.

It is certified that error appears in the above-identified patent and that said Letters Patent is hereby corrected as shown below:

Claim 1,
Line 3, after -- least -- and before -- channel --, delete "on" and insert -- one --

Signed and Sealed this

First Day of January, 2002

Attest:

Attesting Officer

JAMES E. ROGAN
Director of the United States Patent and Trademark Office